(12) United States Patent
Ling et al.

(10) Patent No.: US 9,291,515 B2
(45) Date of Patent: Mar. 22, 2016

(54) RAPID TEST DEVICE

(75) Inventors: Shisheng Ling, Zhejiang (CN); Xuehao Ji, Zhejiang (CN); Keyuan Yao, Zhejiang (CN)

(73) Assignee: ASSURE TECH. (HANGZHOU) CO., LTD., Hangzhou, Zhejiang (CN)

( * ) Notice: Subject to any disclaimer, the term of this patent is extended or adjusted under 35 U.S.C. 154(b) by 286 days.

(21) Appl. No.: 13/978,794

(22) PCT Filed: Apr. 22, 2011

(86) PCT No.: PCT/CN2011/073169
§ 371 (c)(1),
(2), (4) Date: Jul. 9, 2013

(87) PCT Pub. No.: WO2012/100464
PCT Pub. Date: Aug. 2, 2012

(65) Prior Publication Data
US 2013/0291659 A1 Nov. 7, 2013

(30) Foreign Application Priority Data
Jan. 24, 2011 (CN) .......................... 2011 1 0025024

(51) Int. Cl.
*G01N 1/10* (2006.01)
*G01L 7/18* (2006.01)
*B01L 3/00* (2006.01)
*G01N 35/00* (2006.01)

(52) U.S. Cl.
CPC . *G01L 7/18* (2013.01); *B01L 3/502* (2013.01); *B01L 2200/0605* (2013.01); *B01L 2200/0689* (2013.01); *B01L 2300/042* (2013.01); *B01L 2300/046* (2013.01); *B01L 2300/0663* (2013.01); *B01L 2400/0457* (2013.01); *B01L 2400/0644* (2013.01); *G01N 2035/00108* (2013.01)

(58) Field of Classification Search
None
See application file for complete search history.

(56) References Cited

U.S. PATENT DOCUMENTS

| 2003/0224474 | A1* | 12/2003 | Litman | C12Q 1/28 435/28 |
|---|---|---|---|---|
| 2004/0002063 | A1* | 1/2004 | Chan et al. | 435/5 |
| 2007/0275475 | A1* | 11/2007 | Liang | 436/165 |
| 2011/0039261 | A1* | 2/2011 | Hillebrand et al. | 435/6 |
| 2011/0107824 | A1* | 5/2011 | Lv | 73/64.56 |

FOREIGN PATENT DOCUMENTS

CN 102539245 B * 11/2013

* cited by examiner

*Primary Examiner* — Andre Allen
(74) *Attorney, Agent, or Firm* — Global IP Services; Tianhua Gu

(57) ABSTRACT

The invention discloses a rapid test device, includes a cup vessel (4), which comprises a first chamber (41) and a dosing piston assembling hole (44) communicating with the first chamber (41); a base (8) fastened at the bottom of the cup vessel (4); a second chamber (81), formed between the base (8) and the cup vessel (4) and communicating with the dosing piston assembling hole (44); a partition (7), arranged in the second chamber (81) and provided with test paper; a dosing piston (6), provided with a dosing slot (61) thereon and provided with a key hole at one end, inserted in the dosing piston assembling hole (44); and a key (1) matching the key hole. In present invention the sample in the dosing slot can be transmitted into the second chamber by rotating the dosing piston. The sample is absorbed by the test paper after flowing by the test paper, and test result appears on the test paper. Since the dosing slot is machined on the dosing piston, the volume of the liquid sample obtained each time is equal and the accuracy of test result is improved. The dosing piston used to obtain the liquid sample is changed from being pushed linearly to being moved rotationally, which makes leak-proof effect better.

10 Claims, 4 Drawing Sheets

RAPID TEST DEVICE

CROSS REFERENCE TO RELATED PATENT APPLICATION

The present application is the US national stage of PCT/CN2011/073169 filed on Apr. 22, 2011 which claims the priority of the Chinese patent application No. 201110025024.9 filed on Jan. 24, 2011, which application is incorporated herein by reference.

FIELD OF THE INVENTION

The present invention relates to liquid sample testing technique, and particularly relates to a rapid test device.

BACKGROUND OF THE INVENTION

The rapid test device can detect the substances contained in the sample quickly and effectively and provide those skilled in the art a basis for qualitative judgment.

There're already many rapid test devices, wherein the most commonly used is test device detecting liquid sample, which prevents those skilled in the art from touching the sample and makes operation simple, and ensures the accuracy of test result.

Such as an announcement of the Chinese patent No. CN1834622A discloses a test device and testing method for detecting analyte in the liquid sample. The test device comprises an opening which leads the liquid sample into a first chamber, and a second chamber communicating with the first chamber through a through-hole. The detecting element is placed in the second chamber. The test device also comprises a third chamber which communicates with the second chamber through a channel. The third chamber includes movable element having first position and second position. The movable element divides the third chamber into section 1 and section 2. The section 1 is provided with an air outlet. The movable element is sealed with wall region of the third chamber to avoid the airiness in the section 1 and the section 2.

The test device comprises three chambers, wherein the third chamber provides power for whole testing. The third chamber increases after piston movement, and leads air into the second chamber, hereafter the air pressure in the second chamber and in the third chamber overall decreases, so that the air pressure difference is formed between the first chamber and the second chamber. The former balance of liquid sample causing by tension is broken, hereafter the liquid sample flows from the first chamber into the second chamber. The liquid sample flows by the test paper provided in the second chamber, and the sample is partially absorbed by the test paper and test result appears on the test paper. However, the movable element of the test device of the art is piston and the silicone seal ring is used, which makes the leak-proof effect weaker. The extracted volume of liquid sample each time is controlled by lifting piston. The extracted volume of liquid sample each time is different, thereby affecting the accuracy of test results.

SUMMARY OF THE INVENTION

In this connection, the present invention provides a rapid test device ensuring the same extracted volume of liquid sample each time, which improves the accuracy of test results.

To fulfill the above objective, the present invention provides following technical solutions: A rapid test device, characterized by comprising cup vessel, provided with a first chamber and a dosing piston assembling hole communicating with the first chamber; a lid, arranged on the open end of the first chamber; a base, fastened at the bottom of the cup vessel; a second chamber, formed between the base and the cup vessel and communicating with the dosing piston assembling hole; a partition, arranged in the second chamber and provided with test paper; a rotatable dosing piston, provided with a dosing slot thereon and provided with a key hole at one end, inserted in the dosing piston assembling hole; and a key matching the key hole. Preferably, wherein the rapid test device, the outer wall of cup vessel adjacent to partition is transparent.

Preferably, wherein the rapid test device includes a seal sleeve, which has shore hardness of 20-60 A, arranged on the outside of the dosing piston. The seal sleeve provided with at least one opening coincides with the open end of the dosing slot.

Preferably, wherein the rapid test device including the seal sleeve, provided with several silicone seal rings along the circumferential direction and axial direction.

Preferably, wherein the rapid test device includes a seal ring, arranged between the lid and the open end of the first chamber.

Preferably, wherein the rapid test device, a seal ring support is placed below the lid of the cup vessel.

Preferably, wherein the rapid test device, characterized in that a storage slot is provided on the top of the lid to store the key.

Preferably, wherein the rapid test device, the one end of the key is provided with rotatable handle and the other end of the key is provided with key end matching the key hole.

Preferably, wherein the rapid test device, the rotatable handle is number 1 shaped.

Preferably, wherein the rapid test device, the seal sleeve is made out of over molding plastic parts, which is coated with TPE, TPR, TPV, TPEE, TPO or silicone-like material thereon.

From the above technical solutions it should be noted, the present invention connects the first chamber with the dosing piston assembling hole communicating with the second chamber; the dosing piston, inserted in the dosing piston assembling hole and provided with a dosing slot thereon. The dosing piston can be rotated by using the key. The liquid sample flows from the first chamber into the dosing slot. By rotating the key, the liquid sample in the dosing slot can be transmitted into the second chamber, wherein the liquid sample flows by the test paper. A part of liquid sample is absorbed by the test paper in the partition, and test result appears on the test paper. Since the dosing slot is machined on the dosing piston, the volume of the liquid sample obtained each time is equal and the accuracy of test result is improved. The dosing piston used to obtain the liquid sample is changed from being pushed linearly to being moved rotationally, which makes leak-proof effect better.

BRIEF DESCRIPTION OF THE DRAWINGS

In order to illustrate embodiments of the invention or the prior art technical solutions more clearly, in the embodiments or in the prior art description required figures are introduced briefly as below. Apparently, the below figures are only some embodiments of the invention. To those ordinary skilled in the art, they can obtain other figures based on these figures without giving creative efforts.

DETAIL DESCRIPTION OF THE INVENTION

The invention discloses a rapid test device, wherein the volume of the liquid sample obtained each time is equal and the accuracy of test result is improved.

The technical solutions in embodiments of the present invention are described clearly and completely as below with help of figures in embodiments of the present invention.

Apparently, the described embodiments are only a part of the embodiments of the present invention, but not all embodiments. Based on the embodiments of the present invention, all other embodiments obtained by those ordinary skilled in the art without giving creative efforts, belonging to the protection scope of the present invention.

Please refer to FIG. 1-FIG. 4.

Figure 1:
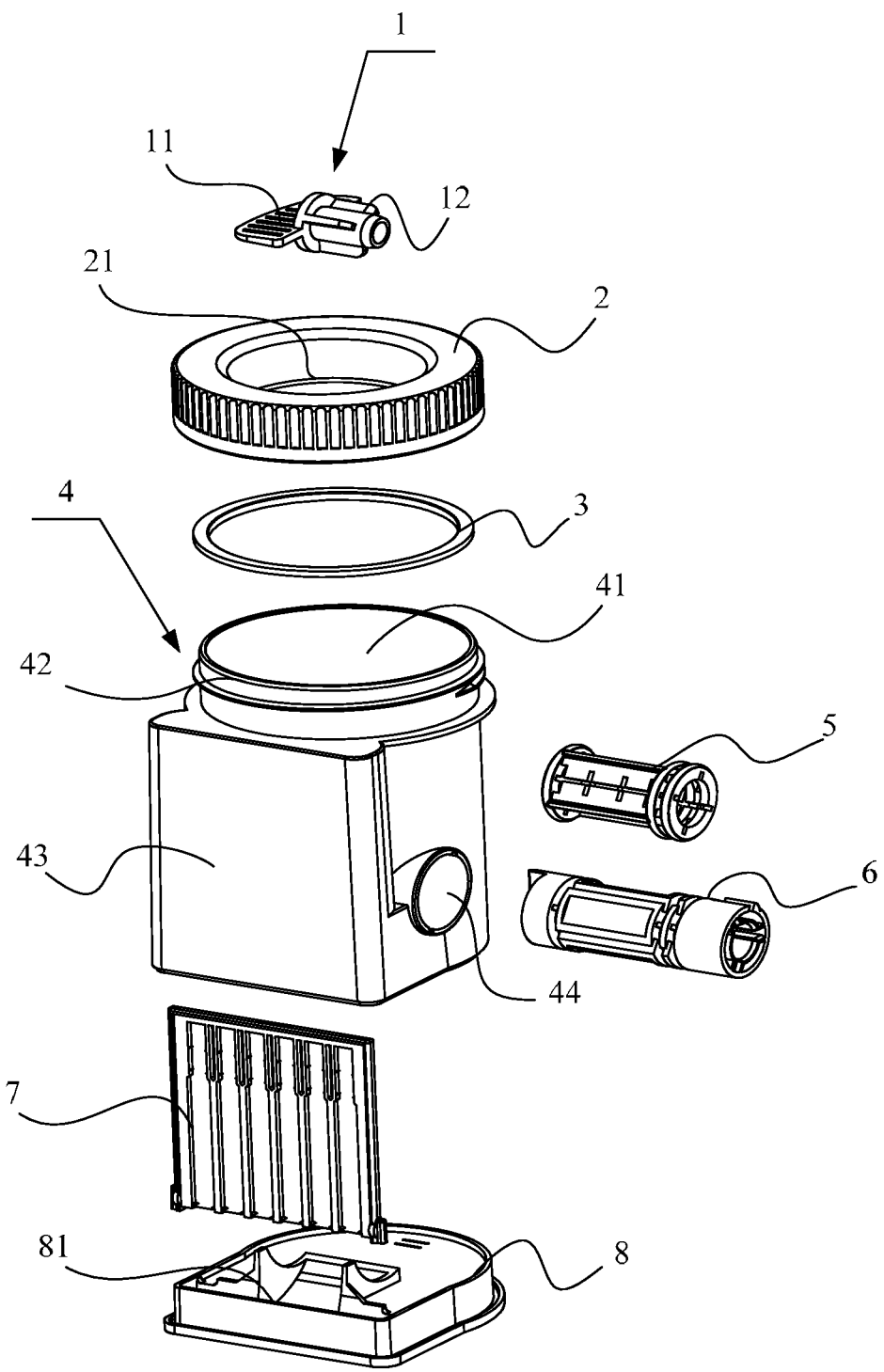
FIG. 1 is breakdown schematic for embodiments of the rapid test device

FIG. 1 is breakdown schematic for embodiments of the rapid test device

Figure 2:
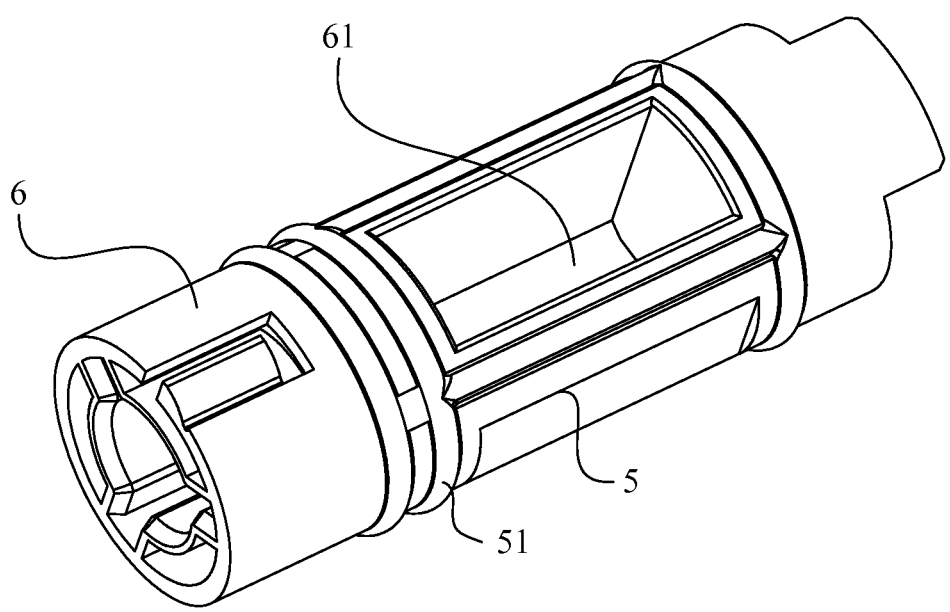
FIG. 2 is structure schematic for dosing piston in embodiments of the present invention
Figure 3:
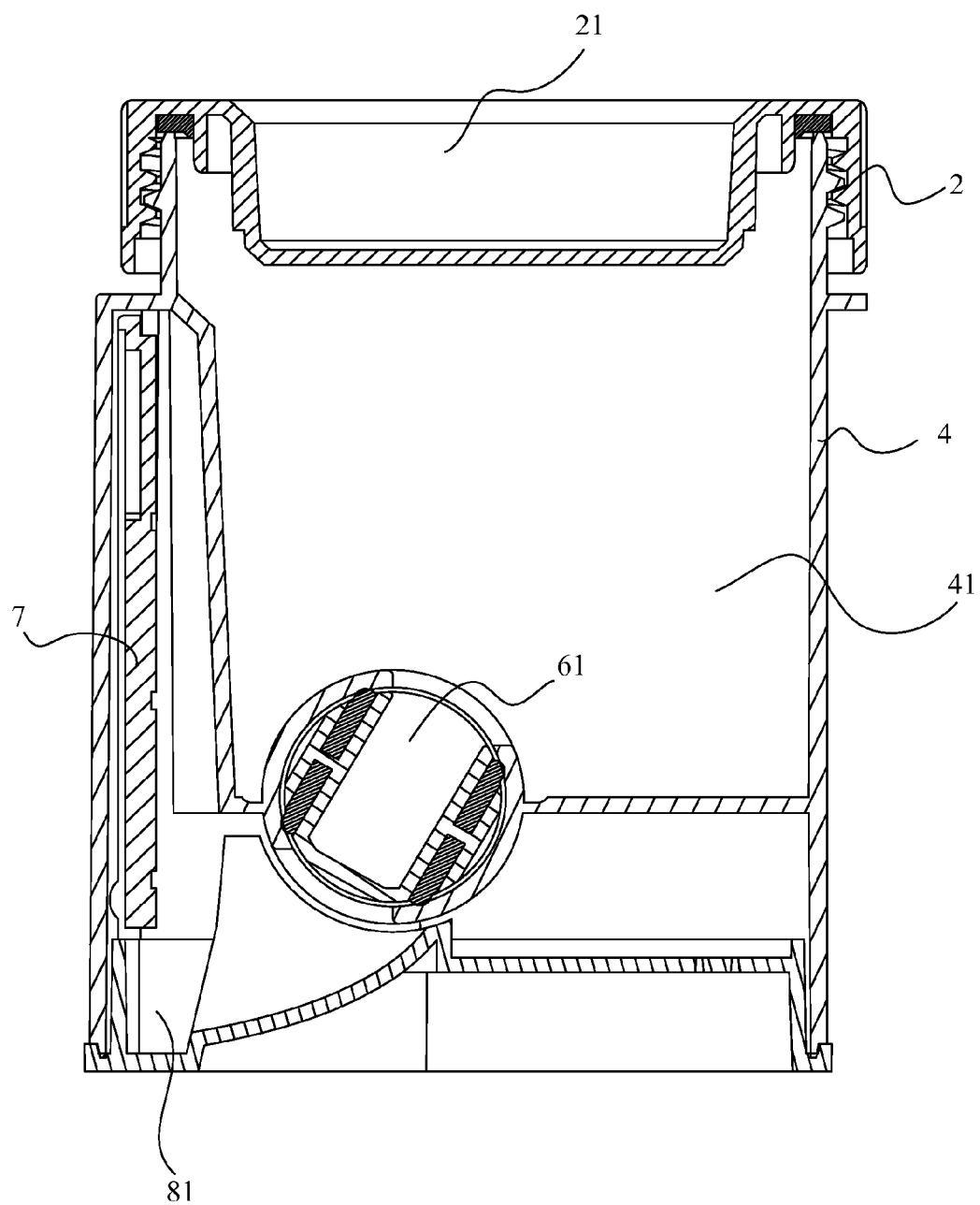
FIG. 3 is side cutaway view in embodiments of the rapid test device
Figure 4:
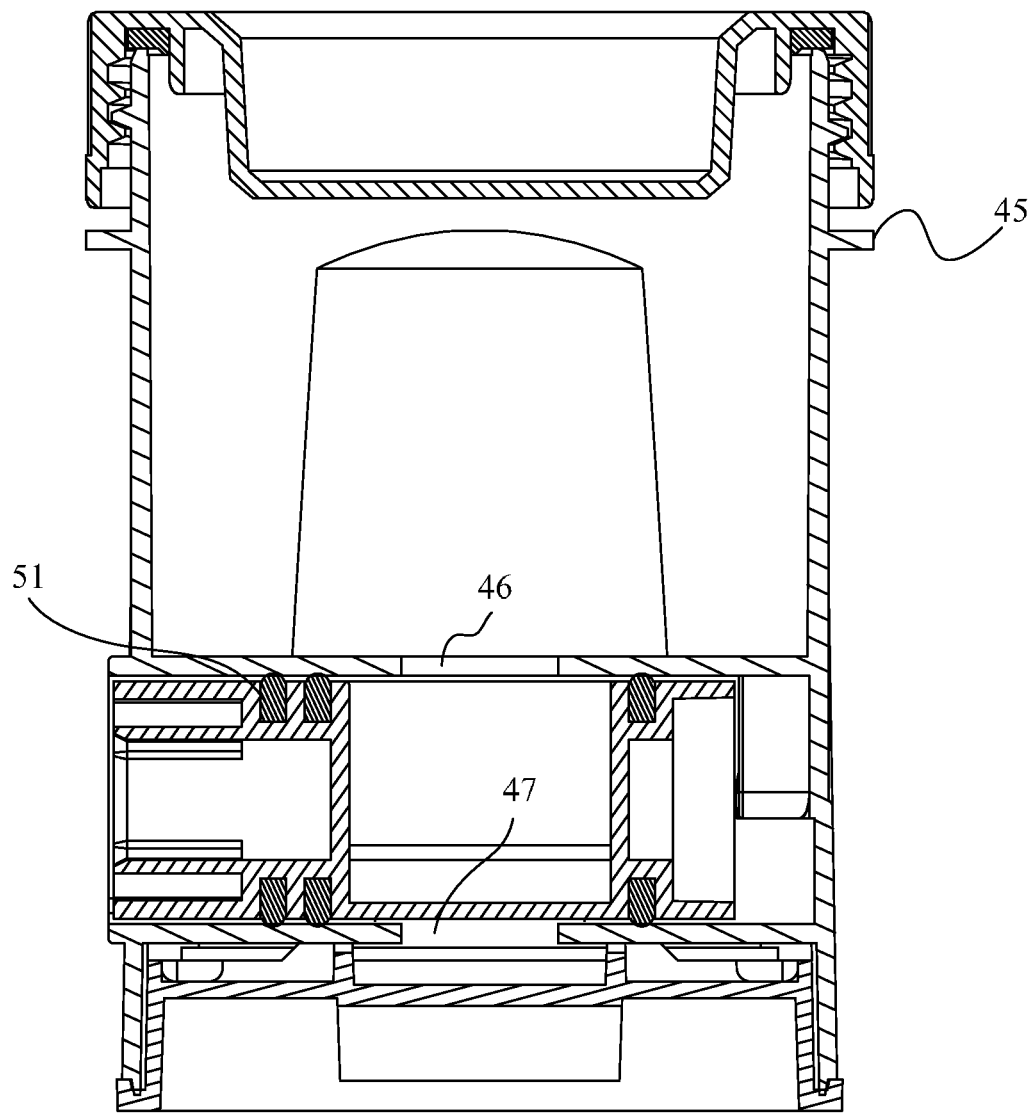
FIG. 4 is rear cutaway view in embodiments of the rapid test device

FIG. 2 is structure schematic for dosing piston in embodiments of the present invention FIG. 3 is side cutaway view in embodiments of the rapid test device FIG. 4 is rear cutaway view in embodiments of the rapid test device The rapid test device of the present invention comprising:

A cup vessel (4); a lid (2); a base (8); a partition (7); a dosing piston (6) and a key (1). Wherein the cup vessel (4) provided with a first chamber (41) and a dosing piston assembling hole (44) communicating with the first chamber (41); a lid (2), arranged on the open end (42) of the first chamber (41). Preferably, the lid (2) screwed firmly on the open end (42) of the first chamber (41), which makes leak-proof effect better; the base (8) formed on the bottom of the cup vessel (4) and assembled by buckling, and a sealing pad arranged in the place of interface for leak-proof purpose; a second chamber (81), formed between the base (8) and the cup vessel (4), and communicated with the dosing piston assembling hole (44). The first chamber and a part of the second chamber is located in the cup vessel (4), wherein the first chamber (41) and the second chamber (81) divided by a division board to prevent the flowing of the liquid sample from the first chamber (41) into the second chamber (81) directly. A partition (7), arranged in the second chamber (81) and provided with test paper. A dosing piston (6), provided with a dosing slot (61) thereon and provided with a key hole at one end, inserted in the dosing piston assembling hole (44); and a key (1) matching the key hole. By inserting the key into the key hole, the dosing piston (6) can be rotated. By rotating the dosing piston (6), the open end of dosing slot (61) matching with the interface between dosing piston assembling hole (44) and the first chamber, and further matching with the interface between the dosing piston assembling hole (44) and the second chamber, thereby transmitting the liquid sample through the dosing slot (61) into the second chamber which is the chamber for testing. The present invention comprises the first chamber (41) and the dosing piston assembling hole (44) communicating with the first chamber (41) and further communicating with the second chamber (81).

The dosing piston (6), provided with a dosing slot (61) thereon, inserted in the dosing piston assembling hole (44). By turning the key (1), the dosing piston (6) can be rotated, thus the liquid sample flows from the first chamber (41) into the dosing slot (61) and the liquid sample can be transmitted from the dosing slot (61) into the second chamber (44) by rotating. The liquid sample flows by the test paper in the second chamber (44) and partially absorbed by the test paper in the partition (7). Test result appears on the test paper. Since the dosing slot (61) is machined on the dosing piston (6), the volume of the liquid sample obtained each time is equal and the accuracy of test result is improved. The dosing piston used to obtain the liquid sample is changed from being pushed linearly to being moved rotationally, which makes leak-proof effect better.

As shown in FIG. 1, the outer wall of cup vessel (4) adjacent to partition (7) is transparent, forming an observation board (43). After testing of liquid sample, the test result can be observed from the observation board (43) without taking out the test paper.

As shown in FIG. 2, in order to optimize the above technical solution, the present invention comprises a seal sleeve (5), which has shore hardness of 20-60 A, arranged on the outside of the dosing piston (6). The seal sleeve (5) provided with at least one opening coincides with the open end of the dosing slot (61). After covering the seal sleeve (5) on the dosing piston (6), the dosing slot (61) in the dosing piston (6) still contacts outside, without blocking the open end of the dosing slot (61). By placing seal sleeve (5) on the dosing piston (6), the interface between the dosing piston assembling hole (44) and the dosing piston consisting of the seal sleeve (5) and the dosing piston (6) is better sealed, thereby improving the leak-proof effect.

Preferably, the seal sleeve (5), provided with several silicone seal rings (51) along the circumferential direction and axial direction. The seal sleeve (5) is made out of over molding plastic parts, which is provided with over molding TYPE (Thermo plastic Elastomer) which means coating thin TYPE on the surface of hard plastic parts through injection molding, TPR (Thermo plastic Rubber), TPV (Thermo Plastic Vulcanizate), TPEE (Thermoplastic Polyeher Ester Elastomer), TPO (Thermoplastic Polyolefin) or silicone-like material thereon, thereby improving the comfort of touch, anti-skidding and buffering performance.

As shown in FIG. 1, the present invention comprises a seal ring (3), arranged between the lid (2) and the open end of the first chamber (41). A seal ring support (45) is placed below the lid (2) of the cup vessel (4). The material of the seal ring (3) can be silicone which prevents leaking from the lid (2). The seal ring support further prevents leaking from the lid (2).

A storage slot (21) is provided on the top of the lid (2) to store the key (1). The key (1) can be stored in the storage slot (21). Certainly, the key (1) can be stored directly in the first chamber (41) or be placed out of the cup vessel (4). Storing the key (1) in the storage slot (21) on the top of the lid (2) doesn't affect testing and losing the key by placing the key (1) out of the cup vessel (4) is avoided.

The one end of the key (1) is provided with rotatable handle (11) and the other end of the key (1) is provided with key end (12) matching the key hole, wherein preferably the rotatable handle (11) is number 1 shaped. Unlike other polygon rotation, the rotatable handle (11) is easy to use.

The present description of each embodiment is described progressively. Each embodiment emphasizes the difference from other embodiments. The similar part of the embodiments can be referred to each other.

The above description for disclosed embodiments enables those skilled in the art to implement or to use the present invention. Various modifications to these embodiments will be apparent for these skilled in the art. The generic principles defined herein may be implemented in other embodiments without departing from the spirit or scope of the present invention. Accordingly, the present invention will not be limited to the embodiments shown herein, but to meet the widest scope consistent with the principles and novel features disclosed herein.

What is claimed is:

1. A rapid test device comprising:
   a cup vessel (4), provided with a first chamber (41) and a dosing piston assembling hole (44) communicating with the first chamber (41);
   a lid (2), arranged on an open end of the first chamber (41);
   a base (8), fastened at a bottom of the cup vessel (4);
   a second chamber (81), formed between the base (8) and the cup vessel (4) and communicating with the dosing piston assembling hole (44);
   a partition (7), arranged in the second chamber (81) and provided with a test paper;
   a dosing piston (6), provided with a dosing slot (61) thereon and provided with a key hole at one end, the dosing piston (6) is inserted in the dosing piston assembling hole (44); and
   a key (1) matching the key hole.

2. The rapid test device claimed in claim 1, wherein an outer wall of the cup vessel (4) adjacent to the partition (7) is transparent.

3. The rapid test device claimed in claim 1, wherein the rapid test device includes a seal sleeve (5), which has shore hardness of 20-60 A, is arranged on outside of the dosing piston (6), the seal sleeve (5) has at least one opening place above open end of the dosing slot (61).

4. The rapid test device claimed in claim 3, wherein the seal sleeve (5) is provided with several silicone seal rings (51) along a circumferential direction and an axial direction.

5. The rapid test device claimed in claim 1, wherein a seal ring (3) is arranged between the lid (2) and an open end of the first chamber (41).

6. The rapid test device claimed in claim 5, wherein a seal ring support (45) is placed below the lid (2) of the cup vessel (4).

7. The rapid test device claimed in claim 1, wherein a storage slot (21) is provided on a top of the lid (2) to store the key (1).

8. The rapid test device claimed in claim 1, wherein one end of the key (1) is provided with a rotatable handle (11) and other end of the key (1) is provided with a key end (12) matching the key hole.

9. The rapid test device claimed in claim 8, wherein the rotatable handle (11) has a straiqht line shape.

10. The rapid test device claimed in claim 3, wherein the seal sleeve (5) is a molding plastic part raped up with thermoplastic elastomers thermoplastic rubber, thermoPlastic vulcanisate, thermoplastic, polyester elastomer, thermoplastic poyolefin, or silicone-like material thereon.

* * * * *